United States Patent [19]
Osugi

[11] Patent Number: 5,416,620
[45] Date of Patent: May 16, 1995

[54] POCKELS CELL WITH AC DRIVING VOLTAGE AT FREQUENCY OF PERIODIC VARIATION OF WRITING LIGHT SOURCE

[75] Inventor: Yukihisa Osugi, Nagoya, Japan
[73] Assignee: NGK Insulators, Ltd., Nagoya, Japan
[21] Appl. No.: 39,794
[22] Filed: Mar. 30, 1993
[30] Foreign Application Priority Data Mar. 30, 1992 [JP] Japan ................................. 4-074393

[51] Int. Cl.$^6$ ........................ G02F 1/135; G02F 1/137
[52] U.S. Cl. ................................. 359/72; 250/214 B;
250/214 C; 250/351; 250/386; 250/387;
345/84; 345/58; 345/87; 359/84; 359/325;
359/245; 348/92; 348/68; 348/752; 348/762
[58] Field of Search .................. 359/72, 84, 325, 245,
359/307; 348/68, 92, 88, 70, 752, 753, 762, 763;
250/386, 387, 227.21, 214 B, 214 C, 351, 347;
345/94, 96, 102, 84, 58, 87

[56] References Cited

U.S. PATENT DOCUMENTS

| | | | |
|---|---|---|---|
| 3,824,008 | 7/1974 | Smith, Jr. ............................. | 359/36 |
| 4,028,544 | 7/1977 | Jourdan et al. .................. | 250/214 B |
| 4,423,927 | 1/1984 | Bly .................................... | 359/72 |
| 4,866,275 | 12/1989 | Jaeger et al. ..................... | 250/351 |
| 4,889,030 | 5/1986 | Kley .................................. | 359/53 |
| 4,922,337 | 5/1990 | Hunt et al. ......................... | 348/92 |
| 5,136,373 | 8/1992 | Kamiya et al. ..................... | 348/92 |
| 5,144,443 | 9/1992 | Takanashi et al. ................. | 359/72 |
| 5,168,528 | 12/1992 | Field, Sr. ........................... | 348/164 |
| 5,170,281 | 12/1992 | Kobayashi et al. ................ | 359/245 |
| 5,221,980 | 6/1993 | Yamamoto et al. ................ | 359/72 |
| 5,303,020 | 4/1994 | Croteau ............................ | 250/214 C |

FOREIGN PATENT DOCUMENTS

0361879A3 4/1990 European Pat. Off. .
2161952 1/1986 United Kingdom .

OTHER PUBLICATIONS

Smith et al, "Real-Time Optical Processing Using the Liquid Crystal Light Valve", J. of App. Photo. Eng., vol. 5, #4, 1979.
Patent Abstracts of Japan, vol. 015, No. 466, (P-1280) & JP-A-03 200 117 (Seiko Epson) 2 Sep. 1991.
Patent Abstracts of Japan vol. 016, No. 451 (P-1424) &JP-A-04 159 514 (Victor Co) 2 Jun. 1992.
Optical Engineering, vol. 17, No. 4, Jul. 1978, Bellingham US pp. 353-364 B.. A. Horwitz, et al. "The Prom-Theory and Applications for the Pockels Readout Optical Modulator".
Optical Engineering, vol. 14, No. 1, May 1975, Bellingham US pp. 217-225 J. Grinberg "A New Real-Time Non-Coherent to Coherent Light Image Converter the Hybrid Field Effect Liquid Crystal Light Valve".
Soviet Physics Technical Physics, vol. 28, No. 6, Jun. 1983, New York US pp. 737-739 E. V. Abel' et al. "Recording of Nonstationary Images by MDSM Photosensitive Structures Containing A Liquid Crystal".
Soviet Journal of Quantum Electronics, vol. 13, No. 6, Jun. 1983, New York US pp. 689-695, A. A. Vasil' EV et al. "Progress in the Development and Applications of Optically Controlled Liquid Crystal Spatial Light Modulators (Review)".
Hou, S. L. and D. S. Oliver, "Pockels Readout Optical Memory Using Bi12Si020", *Applied Physics Letters*, vol. 18, No. 8, p. 325, 1971.
Barrett, H. H., A. F. Gmitro and M. Y. Chiu, "Use of an Image Orthicon As An Array of Lock-in Amplifiers", *Optics Letters*, vol. 6, No. 1, p. 1 1981.

*Primary Examiner*—William L. Sikes
*Assistant Examiner*—Kenneth Parker
*Attorney, Agent, or Firm*—Adduci, Mastriani, Schaumberg & Schill

[57] ABSTRACT

Disclosed is a picture information memory device, including a picture information memory means for generating electric charges corresponding to the intensity of write-in light incident thereon, and for holding the generated electric charges as polarized charges, an exposing means for exposing the picture information memory means to light from an object, and an alternating-current bias voltage applying means for applying an alternating-current bias voltage having a desired frequency to the picture information memory means, whereby electric charges generated by the portion of the object light the intensity of which varies at the same frequency as that of the alternating-current bias voltage, are selectively accumulated from the entirety of electric charges generated by the object light incident on the picture information memory means, and held as the polarized charges in the picture information memory means.

17 Claims, 6 Drawing Sheets

FIG.5

POCKELS CELL WITH AC DRIVING VOLTAGE AT FREQUENCY OF PERIODIC VARIATION OF WRITING LIGHT SOURCE

BACKGROUND OF THE INVENTION

1. Field of the invention

The present invention relates to a picture information memory device and a picture information reproducing device, and more particularly, to a picture information memory device using a Pockels Readout Optical Modulator (PROM) element and capable of selectively and optically recording picture information which repeatedly appears at a regular period, and to a picture information reproducing device for reproducing the picture information recorded in the picture information memory device.

2. Description of the Related Art

Various picture information memory devices, such as a camera tube, a two-dimensional CCD array, have heretofore been put to practical use. In such devices, light from an object to be recorded is converted into electric signals to record and reproduce a picture of the object.

There is a strong demand for selectively, from the entire incident image, recording an image produced from the light which repeatedly appears at a regular period, e.g., an image produced from light emitted and flashed at the regular period. For example, there is a strong demand for development of picture information memory devices capable of clearly recording spark discharge patterns which occur at an insulator connecting portion and a transformer both employed in a high-voltage transmission line. In picture information memory devices which are now put to practical use, however, the entire light incident on a photoelectric converter portion, are photoelectrically converted, and therefore both the light produced by a spark discharge and the light from the background are photoelectrically converted. Therefore, an image produced by the spark discharge are superimposed on a background image, thereby making it impossible to clearly record only the image produced by the spark discharge.

A PROM element of a spatial light modulator, has already been known as a picture information memory device. Here, the PROM element is defined as an element which generates electric charges corresponding to the intensity of write-in light incident thereon due to an photoconductive effect, holds the generated electric charges as polarized charges, and varies the polarization state of readout light incident thereon according to the polarized charges due to the Pockels effect. The PROM element includes, for example, a $Bi_{12}SiO_{20}$ single crystal plate. Picture information is written into the PROM element by using a photoconductive effect, and the picture information is read therefrom by using the Pockels effect.

That is, in writing the picture information into the PROM element, the PROM element is irradiated with write-in light with a direct-current bias voltage being applied to the PROM element, thereby forming polarized charges corresponding to the picture information inside the PROM element so as to record the picture information therein. When the recorded picture information is read, linearly polarized light is projected onto the PROM element under a direct-current biased state or a non-biased state, thereby reading the picture information from the PROM element by making use of the Pockels effect based on the polarized charges formed inside the PROM element. When a picture information memory and reproducing device using the PROM element is used, an incoherent optical image can be converted into a coherent optical image, and the optical image can be subjected to an optical Fourier conversion. Thus, various advantages can be achieved in an image analysis.

When the above-described PROM element is used as a picture information recording medium, various optical image information processings can be effected to the recorded image. Thus, if only a picture repeatedly appearing at a specific frequency, of various incident pictures, can be recorded in the PROM element, various advantages in terms of the image analysis can be achieved as well as the recording of a periodically-appearing picture in the PROM element.

In the conventional picture information memory device for recording the picture information in the PROM element, however, both a background image and an image appearing at a regular period are recorded in the PROM element in a superimposed state. It is, therefore, impossible to selectively record the image appearing repeatedly at a regular period. As a result, the periodic image cannot be selectively and clearly recorded and reproduced.

SUMMARY OF THE INVENTION

It is, therefore, an object of the present invention to provide a picture information memory device capable of selectively recording into a PROM element, an image repeatedly appearing at a specific period, from various incident images, and a picture information reproducing device for reproducing the picture information recorded in the picture information memory device.

According to one aspect of the present invention, there is provided a picture information memory device, comprising:
- picture information memory means for generating electric charges corresponding to the intensity of write-in light incident thereon, and for holding the generated electric charges as polarized charges;
- exposing means for exposing the picture information memory means to light from an object; and
- alternating-current bias voltage applying means for applying an alternating-current bias voltage having a desired frequency to the picture information memory means,
- whereby electric charges generated by the portion of the object light the intensity of which varies at the same frequency as that of the alternating-current bias voltage, are selectively accumulated from the entirety of electric charges generated by the object light incident on the picture information memory means, and held as the polarized charges in the picture information memory means.

According to another aspect of the present invention, there is provided a picture information reproducing device, comprising:
- a spatial light modulating means for generating electric charges corresponding to the intensity of write-in light incident thereon, for holding the generated electric charges as polarized charges, and for modulating readout light incident thereon according to the polarized charges;

first exposing means for exposing the spatial light modulating means to light from an object;

alternating-current bias voltage applying means for applying an alternating-current bias voltage having a desired frequency to the spatial light modulating means;

second exposing means for exposing the spatial light modulating means to readout light; and readout light detecting means for detecting the readout light emitted from the spatial light modulating means, whereby electric charges generated by the portion of the object light the intensity of which varies at the same frequency as that of the alternating-current bias voltage, are selectively accumulated from the entirety of electric charges generated by the object light incident on the spatial light modulating means, and held as the polarized charges in the spatial light modulating means, and picture information from the portion of the object light the intensity of which varies at the same frequency as that of the alternating-current bias voltage is selectively detected by detecting the emitted readout light modulated according to the polarized charges.

The picture information memory device and the picture information reproducing device may further comprise frequency detecting means for detecting an intensity-changing frequency of a portion of the object light, the intensity of which varies at a certain frequency, and the alternating-current bias voltage applying means applies an alternating-current bias voltage having the same frequency as the intensity-changing frequency.

The picture information memory device and the picture information reproducing device may further comprise phase adjusting means for adjusting the phase of the alternating-current bias voltage.

The picture information memory device and the picture information reproducing device may further comprise direct-current bias voltage applying means for applying a direct-current bias voltage to the picture information memory means or the spatial light modulating means.

As the picture information memory means or the spacial light modulating means, spatial light modulating means for generating electric charges corresponding to the intensity of write-in light incident thereon, for holding the generated electric charges as polarized charges, and for varying the polarization state of readout light incident thereon according to the polarized charges, may be used.

As the spacial spatial light modulating means, an element for generating electric charges corresponding to the intensity of write-in light incident thereon due to a photoconductive effect, for holding the generated electric charges as polarized charges, and for varying the polarization state of readout light incident thereon according to the polarized charges due to the Pockels effect, may be used.

The picture information memory device and the picture information reproducing device may further comprise a liquid crystal layer capable of changing the polarization state or the transmissivity of the readout light according to the polarized charges, in addition to the element for generating electric charges corresponding to the intensity of write-in light incident thereon due to a photoconductive effect, for holding the generated electric charges as polarized charges, and for varying the polarization state of readout light incident thereon according to the polarized charges due to the Pockels effect.

As the spatial light modulating means, spatial light modulating means for generating electric charges corresponding to the intensity of write-in light incident thereon, for holding the generated electric charges as polarized charges, and for varying the transmissivity of readout light incident thereon according to the polarized charges, may also be used.

The picture information memory means or the spatial light modulating means may comprise a memory layer of a material having a photoconductive effect and a readout layer of a liquid crystal.

When write-in light of an intensity I is perpendicularly projected onto falls on a certain crystal plane of a photoconductive material such as a PROM element, the quantity of charges Q accumulated on the crystal plane of the PROM element is given by the following equation using a current i(t) which flows in the crystal of the PROM element along the direction orthogonal to the crystal plane.

$$N = \int i(t) dt \qquad (1)$$

The current i(t) is represented by the product of a charge density q(t) of carriers excited by the write-in light and a travelling speed of the carrier. Because the travelling speed is proportional to an applied electric field E(t), the current i(t) is given by the following equation, assuming that a bias voltage applied to the PROM element is V(t).

$$i(t) \propto q(t) E(t) \propto q(t) V(t) \qquad (2)$$

Further, the charge density q(t) of the carrier is proportional to an intensity I(t) of the write-in light as follows:

$$q(t) \propto I(t) \qquad (3)$$

Accordingly, the quantity of the charges Q accumulated on the crystal plane of the PROM element is represented by the following equation:

$$Q \propto \int I(t) V(t) dt \qquad (4)$$

Let's first consider where a direct-current bias voltage V(t) is applied to the PROM element. Since, in this case, the bias voltage V(t) is constant, the equation (4) is rewritten as follows:

$$Q \propto V \int I(t) dt \qquad (5)$$

The quantity of the charges Q accumulated on the crystal plane of the PROM element is proportional only to the time integral of the intensity I(t) of the write-in light, and does not depend on a time-variation component of the write-in light.

Let's next consider where an alternating-current bias voltage $V(t) = V_o \cos 2\pi \omega t$ is applied to the PROM element.

Assuming that the intensity I(t) of the write-in light is represented as $I(t) = I_o(\cos 2\pi \omega t + 1)$, the quantity of charges Q accumulated on the crystal plane of the PROM element is Given by the following equation:

$$Q \int I_o V_o \int \cos 2\pi \omega t (\cos 2\pi \omega' t + 1) dt \qquad (6)$$

When the write-in light is continuous light whose intensity is constant with respect to the time, that is, when $\omega'=0$, the equation (6) is rewritten as follows:

$$Q \propto 2I_oV_o\cos2\pi\omega t dt = (I_oV_o/\pi\omega)\sin(2\pi\omega t) \tag{7}$$

As is apparent from the equation (7), when the alternating-current bias voltage is applied to the PROM element, even though the PROM element is irradiated with the continuous light, a slight increase and a slight decrease in the quantity of the charges Q accumulated on the crystal plane of the PROM element are simply repeated. Thus, when the alternating-current bias voltage is applied to the PROM element, the PROM element is almost insensitive to the continuous light.

Next, when the frequency of the write-in light is the same as the frequency of the alternating-current bias voltage applied to the PROM element, that is, when $\omega'=\omega$, the equation (6) is rewritten as follows:

$$Q \propto I_oV_o\int\cos2\pi\omega t(\cos2\pi\omega t + 1)dt = \tag{8}$$
$$I_oV_o((t/2) + (1/2\pi\omega)\sin2\pi\omega t + (1/8\pi\omega)\sin4\pi\omega t)$$

The first term in the equation (8) is proportional to the product of an $I_o$ component of the intensity I(t) of the write-in light and a $V_o$ component of the alternating-current bias voltage V(t). Thus, when the alternating-current bias voltage is applied to the PROM element, if the frequency of the write-in light is equal to that of the alternating-current bias voltage, electric charges corresponding to the intensity of the write-in light are accumulated on the crystal plane of the PROM element. As a result, the PROM element is made sensitive to the light whose intensity varies in synchronism with the alternating-current bias voltage.

As explained above, when the alternating-current bias voltage is applied to the PROM element, the PROM element is insensitive to the continuous light but sensitive to the light whose intensity varies in synchronism with the alternating-current bias voltage. Thus, when the light incident on the PROM element from an object consists of the continuous light and the light whose intensity varies in synchronism with the alternating-current bias voltage, electric charges produced by the light whose intensity changes in synchronism with the alternating-current bias voltage can be selectively accumulated on the crystal plane of the PROM element. Therefore, picture information which is in synchronism with the alternating-current bias voltage applied to the PROM element, can be selectively recorded in the PROM element.

When a plurality of pieces of picture information which appear at various periods, is projected onto the PROM element, the picture information synchronized with the applied alternating-current bias voltage is selectively recorded in the PROM element. Accordingly, by varying the frequency of the alternating-current bias voltage applied to the PROM element, only the picture information whose frequency is identical to that of the alternating-current bias voltage, can be recorded in the PROM element selectively from the plurality of pieces of picture information varied at various frequencies.

Moreover, by further providing a frequency detecting means for detecting an intensity-changing frequency of the portion of the object light the intensity of which varies at a certain frequency, and by applying an alternating-current bias voltage having the same frequency as the intensity-changing frequency by the alternating-current bias voltage applying means, the picture information the intensity of which varies at the intensity-changing frequency can be selectively recorded more effectively.

Moreover, background picture information as well as the picture information whose intensity level varies at the regular frequency can also be recorded in a superimposed state by providing the direct-current bias voltage applying means capable of applying the direct-current bias voltage to the PROM element in addition to the alternating-current bias voltage applying means. It is, therefore, possible to accurately recognize the position of the picture whose intensity level varies at the regular frequency in the object.

After the alternating-current bias voltage has been applied to the PROM element and the picture information whose intensity varies at the regular frequency has been selectively recorded in the PROM element, the direct-current bias voltage may be applied to the PROM element so as to record the background picture information in the PROM element in a state superimposed on the picture information whose intensity varies at the regular frequency. Alternatively, the alternating-current bias voltage and the direct-current bias voltage may be simultaneously applied to the PROM element so that the selective recording of the picture information whose intensity varies at the regular frequency to the PROM element and the recording of the background picture information to the PROM element are simultaneously effected.

Even when a phase difference $\phi$ exists between the picture information whose intensity level varies at a regular frequency and an alternating-current bias voltage, the selective recording of the picture information whose intensity varies at the regular frequency can be effectively carried out by further providing the phase adjusting means for adjusting the phase of the alternating-current bias voltage.

When the phase difference $\phi$ exists between the write-in light: $I(t)=I_o(\cos2\pi\omega+1)$ and the alternating-current bias voltage: $V(t)=V_o\cos2\pi\omega t$, the equation (6) is represented as follows:

$$Q \propto I_oV_o\int\cos2\pi\omega t(\cos(2\pi\omega t + \phi) + 1)dt = \tag{9}$$
$$I_oV_o((1/2)\cos\phi \cdot t + (1/2\pi\omega)\sin2\pi\omega t + (1/8\pi\omega)\sin(4\pi\omega t + \phi))$$

The first term in the equation (9) is proportional to the product of the time t, the $I_o$ component of the intensity I(t) of the write-in light, the $V_o$ component of the alternating-current bias voltage V(t) and $\cos\phi$. Thus, even when the frequency of the write-in light is equal to that of the alternating-current bias voltage, the sensitivity of the PROM element depends on the phase difference $\phi$ between the write-in light and the alternating-current bias voltage. When the phase difference $\phi$ is $\pi/2$ or $3/2\cdot\pi$, the PROM element is insensitive to the light whose intensity varies at the same frequency as that of the alternating-current bias voltage. When, on the other hand, the phase difference $\phi$ is not $\pi/2$ or $3/2\cdot\pi$, the PROM element is sensitive to the light whose intensity varies at the same frequency as that of the alternating-current bias voltage. When the phase difference $\phi$ is the value which makes the value of $|\cos\phi|$ is set to be $|\cos\phi|=1$, the sensitivity of the PROM element reaches the maximum.

Accordingly, the selective recording of the picture information whose intensity varies at the regular frequency can be effectively carried out by further providing the phase adjusting means capable of varying the phase of the alternating-current bias voltage applied to the PROM element by the alternating-current bias voltage applying means and adjusting the phase difference φ.

In the foregoing, the picture information recording operation is explained by taking the PROM element having both the photoconductive effect and the Pockels effect as an example of the picture information memory means for generating electric charges corresponding to the intensity of write-in light incident thereon, and for holding the generated electric charges as polarized charges, and as an example of the spatial light modulating means for generating electric charges corresponding to the intensity of write-in light incident thereon, for holding the generated electric charges as polarized charges, and for modulating readout light incident thereon according to the polarized charges. However, when a material which has the photoconductive effect and does not have the Pockels effect, such as a GaAs single crystal, a GaAs film, a hydrogenated amorphous silicon film, an amorphous silicon carbide film and amorphous selenium film, is used as a recording material for the picture information memory means and for the spatial light modulating means, the same picture information recording function is performed as when the PROM element is used.

As a spatial light modulating means used in the picture information reproducing device, the spatial light modulating means which generates electric charges corresponding to the intensity of write-in light incident thereon, holds the generated electric charges as polarized charges, and varies the polarization state of readout light incident thereon according to the polarized charges, may be used.

As this kind of spatial light modulating means, a PROM element can be cited as an example. As described above, the PROM element is an element which generates electric charges corresponding to the intensity of write-in light incident thereon due to a photoconductive effect, holds the generated electric charges as polarized charges, and varies the polarization state of readout light incident thereon according to the polarized charges due to the Pockels effect. Therefore, when the PROM element is used as a picture information recording material, the PROM element itself can change the polarization state of readout light, and therefore there is no need to provide an additional readout material in addition to the recording material.

A liquid crystal material can also be used as a readout material which varies the polarization state of readout light according to the polarized charges.

When a liquid crystal, such as a twisted nematic liquid crystal (TNLC), which varies the polarization state of readout light incident thereon according to the applied voltage, is further provided in addition to the PROM element, a voltage value of an alternating-current bias voltage applied to the PROM element upon writing can be reduced. Thus, the alternating-current bias voltage applying means can be simplified in structure. The applied voltage required to obtain the same varied polarization state of readout light is lowered by two orders of magnitude or more when the liquid crystal is used as compared with when only the PROM element is used. Therefore, even if the voltage value of the alternating-current bias voltage applied to the PROM element upon write-in is lowered to reduce the quantity of the electric charges accumulated and held on the crystal planes of the PROM element, the polarization state of the readout light can be varied as much as needed by the liquid crystal by applying an electric field produced by the reduced amount of the electric charges to the liquid crystal.

When a material which has a photoconductive effect but does not have the Pockels effect, such as a GaAs single crystal, a GaAs film, a hydrogenated amorphous silicon film, an amorphous silicon carbide film and an amorphous selenium film, is used as a recording material for the picture information memory means and for the spatial light modulating means, a liquid crystal, such as a twisted nematic liquid crystal (TNLC), which varies the polarization state of readout light incident thereon according to the applied voltage, can be used as a readout material. Also in this case, because the desired polarization state of the readout light can be obtained by a small applied voltage, the voltage value of the high voltage bias voltage applied to the recording material can be reduced, thereby the alternating-current bias voltage applying means can be simplified in structure.

When the spatial light modulating element which generates electric charges corresponding to the intensity of write-in light incident thereon, holds the generated electric charges as polarized charges, and varies the polarization state of readout light incident thereon according to the polarized charges, is used as the spatial light modulating means, a device using a polarizer or the like to make linearly polarized light to be directed onto the PROM element may preferably be used as a read-in light directing means which is provided in the picture information reproducing device to cause the read-in light to be directed onto the PROM element, and a device having an element such as an analyzer or the like capable of detecting the polarization state of light may preferably be used as a readout light detecting means for detecting the readout light emitted from the PROM element.

As the spatial light modulating means used in the picture information reproducing means, a spatial light modulating means for generating electric charges corresponding to the intensity of write-in light incident thereon, for holding the generated electric charges as polarized charges, and for varying the transmissivity of readout light incident thereon according to the polarized charges, may also be used.

As a readout material varying the transmissivity of readout light incident thereon according to the polarized charges, a liquid crystal material can be cited as an example. When a liquid crystal, such as a polymer dispersed liquid crystal (PDLC), which varies the transmissivity of readout light according to the applied voltage, is used as the liquid crystal, it becomes unnecessary to use the polarized light as the readout light. Therefore, a polarizer and an analyzer become unnecessary, thereby making it possible to simplify the structure of the picture information reproducing device.

The liquid crystal, such as a polymer dispersed liquid crystal (PDLC), which varies the transmissivity of readout light according to the applied voltage, may be provided in addition to the PROM element, and may also be used as a readout material when a material which has a photoconductive effect but does not have the Pockels effect, such as a GaAs single crystal, a GaAs film, a hydrogenated amorphous silicon film, an amorphous silicon carbide film and amorphous selenium film, is used as a recording material for the picture information memory means and for the spatial light modulating means.

Let's next consider a write-in time TW for picture information. When the frequency of the picture information coincides with that of the alternating-current bias voltage, the write-in time TW can be set to be any values. When, on the other hand, a deviation is developed between the frequency $\omega'$ of the picture information and the frequency $\omega$ of the alternating-current bias voltage, how to set the write-in time TW becomes a problem.

Let's now consider when $\omega' \neq \omega$ in the equation (6).

$$Q \propto I_0 V_0 \int (\cos 2\pi \omega t + \cos 2\pi \omega t \cdot \cos 2\pi \omega' t) dt = \quad (10)$$
$$I_0 V_0 ((1/2\pi\omega)\sin 2\pi\omega t + (1/2\pi(\omega + \omega'))\sin 2\pi(\omega + \omega')t + (1/2\pi(\omega - \omega'))\sin 2\pi(\omega - \omega')t)$$

When $\omega \sim \omega'$, the third term in the equation (10) varies more slowly than the other terms and has a large amplitude. Thus, when the write-in of the picture information into the PROM element is completed at a period faster than the period of the third term, the picture information can be recorded in the PROM element. When, in this case, the write-in time TW is set so as to meet the following equation, then the PROM element is made sensitive.

$$\omega - \omega' < 1/TW \quad (11)$$

BRIEF DESCRIPTION OF THE DRAWINGS

The above and further objects, features and advantages of the present invention will become more apparent from the following detailed description taken in conjunction with the accompanying drawings, wherein.

DETAILED DESCRIPTION OF THE PREFERRED EMBODIMENTS

Figure 1:
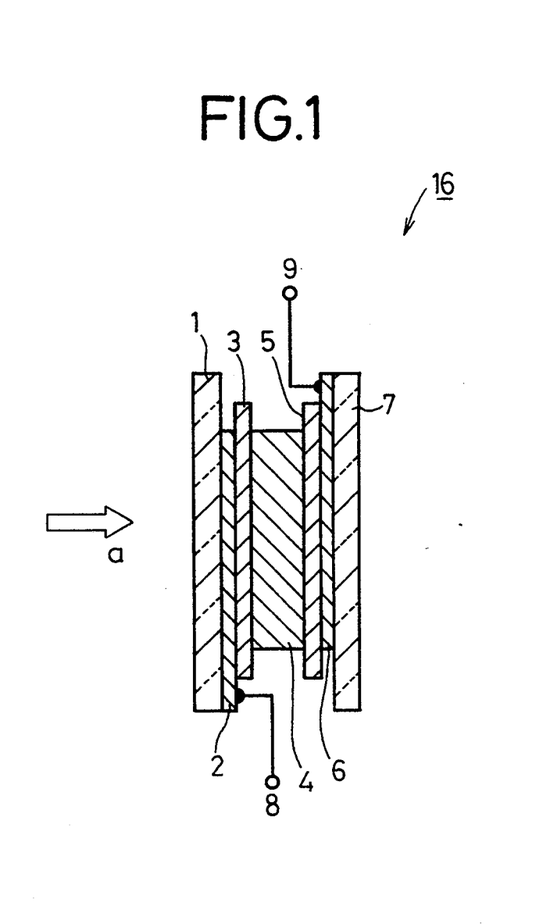
FIG. 1 is a cross-sectional view for explaining a PROM element used for a picture information memory device and a picture information reproducing device according to the present invention.

Referring to FIG. 1, in a PROM element 16, insulating layers 3 and 5 made of a quartz glass are respectively disposed on both sides of an electric charge generating and holding layer 4 made of a single crystal of $Bi_{12}SiO_{20}$. Further, transparent electrodes 2 and 6 made of ITO (Indium Tin Oxide) are disposed outside the insulating layers 3 and 5, respectively. Furthermore, substrate glasses 1 and 7 made of quartz glass are disposed on the outsides of the transparent electrodes 2 and 6, respectively.

Picture information write-in light is directed onto the PROM element 16 from the direction indicated by the arrow a. Because $Bi_{12}SiO_{20}$ is a sensitivity (photoconductivity) to an electromagnetic wave whose wavelength is equal to or shorter than that of blue light, light in a blue region, X-rays, etc. are used as the write-in light. When the write-in light is directed onto the PROM element 16, charge carriers (electrons and holes) corresponding to the intensity of the write-in light are generated in the charge generating and holding layer 4 by a photoconductive effect. When a bias voltage is applied between the transparent electrodes 2 and 6 through terminals 8 and 9, the charge carriers generated by the photoconductive effect drift within the charge generating and holding layer 4 by an electric field formed in the charge generating and holding layer 4 so as to be polarized on the surface of the charge generating and holding layer 4. The charges thus polarized are held on both surfaces of the charge generating and holding layer 4 as the polarized charge because the insulating layers 3 and 5 are disposed on both surfaces of the charge generating and holding layer 4.

In the present invention, an alternating-current bias voltage of a frequency corresponding to a frequency of picture information to be recorded is applied between the transparent electrodes 2 and 6. The alternating-current bias voltage may be any of those having various waveforms such as a sinusoidal wave, a triangular wave, a rectangular wave. The alternating-current bias voltage having a frequency corresponding to the frequency of the picture information is applied, charges proportional to the light intensity of the picture information, i.e., the intensity of the incident light is held on the surface of the charge generating and holding layer 4 as the polarized charges. Therefore, the amount of the polarized charge and its spacial distribution are recorded in the PROM element 16 as picture information.

As explained above, because the amount of the polarized charge and its spacial distribution are recorded in the PROM element 16, picture information having a gradation characteristic is recorded in the PROM element 16.

The picture information recorded in the PROM element 16, can be erased by simply exposing the PROM element 16 to the electromagnetic wave whose wavelength is equal to or shorter than that of blue light with the transparent electrodes 2 and 6 have been short-circuited.

When the polarized charges are formed on the surface of the $Bi_{12}SiO_{20}$ single crystal, an electric field having a strength corresponding to the polarized charges are produced, thereby generating a double refractive characteristic in the $Bi_{12}SiO_{20}$ crystal. Thus, in reproducing the recorded picture information, when the PROM element 16 is exposed to linearly polarized readout light, elliptically polarized light corresponding to the amount of the polarized charge is emitted from the PROM element 16. Therefore, if an analyzer is placed in a subsequent stage, then the amount of the polarized charge can be measured by measuring the intensity of light emitted from the analyzer. Accordingly, the picture information which has been recorded in the PROM element 16, can be reproduced as an optical image by projecting the light emitted from the analyzer onto a screen subsequent to the analyzer through an image formation optical system. At this time, if the light which does not cause the photoconductive effect on the $Bi_{12}SiO_{20}$ single crystal, for example, red light, is used as the readout light, the reproducing of the picture information can be effected without changing the distribution state of the polarized charges.

When the picture information is reproduced, a direct-current bias voltage may be applied between the transparent electrodes 2 and 6 of the PROM element 16. Alternatively, the transparent electrodes 2 and 6 may be short-circuited to each other. When the direct-current bias voltage is applied between the transparent electrodes 2 and 6, an external electric field formed by the direct-current bias voltage is compensated by the electric field produced by the polarized charges. Thus, in the charge generating and holding layer 4, the portion which has been irradiated with the write-in light, is subjected to a weak electric field, whereas the portion which has not been irradiated with the write-in light, is subjected to a strong electric field. The picture to be read becomes a negative image of the written picture information. When the transparent electrodes 2 and 6 are short-circuited to each other, only the electric filed produced by the polarized charge exists in the charge generating and holding layer 4. As a result, the electric fields become strong at the portion irradiated with the write-in light and weak at the portion unirradiated with the write-in light. Thus, the picture to be read becomes a positive image of the written picture information.

The image reproduced from the PROM element 16 can be recorded by a TV camera so as to be displayed on a CRT, for example. Alternatively, the reproduced image can also be projected and displayed on the screen through a projecting lens system. Further, an optical system used for optical image processing such as optical Fourier transformation may be provided if necessary, and the image reproduced from the PROM element 16 may be input to the optical system so as to be subjected to the suitable image processing.

Figure 2:
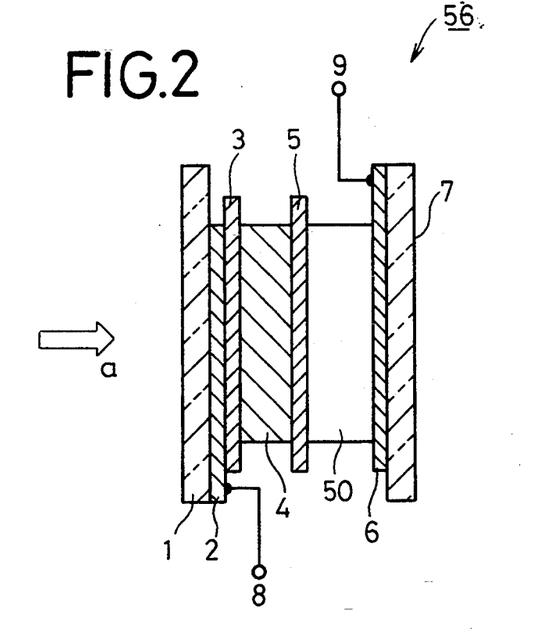
FIG. 2 is a cross-sectional view for explaining a PROM element with a liquid crystal used for a picture information memory device and a picture information reproducing device according to the present invention.

Referring to FIG. 2, a liquid crystal layer 50 is disposed between the insulating layer 5 and the transparent electrode 6. When a material, such as a twisted nematic liquid crystal (TNLC), which varies the polarization state of readout light according to an applied voltage, is used as a liquid crystal layer 50, the voltage value of an alternating-current bias voltage applied between the transparent electrodes 2 and 6 of a PROM element 56 with liquid crystal upon write-in can be reduced. Thus, an alternating-current bias applying device for applying the alternating-current bias voltage can be simplified in structure and reduced in cost. The applied voltage required to obtain the same varied polarization state is lowered by two orders of magnitude or more in the case of the liquid crystal as compared with the PROM element 16 shown in FIG. 1. Therefore, even if the voltage value of the alternating-current bias voltage applied between the transparent electrodes 2 and 6 of the PROM element 56 with liquid crystal upon write-in is reduced and the amount of electric charges accumulated and held on crystal planes of a charge generating and holding layer 4 is reduced, the polarization state of the readout light can be varied as much as needed by the liquid crystal layer 50 by applying an electric field produced by the reduced amount of the electric charges to the liquid crystal layer 50.

Furthermore, in the elements of this structure, it is the liquid crystal layer 50 that modulates the readout light, and therefore, a material which has a photoconductive effect and does not have the Pockels effect may also be used as the charge generating and holding layer 4. Therefore, as the charge generating and holding layer 4, a GaAs single crystal, a GaAs film, a hydrogenated amorphous silicon film, an amorphous silicon carbide film and an amorphous selenium film may also be used.

When a material such as a polymer dispersed liquid crystal (PDLC), which varies the transmissivity Of the readout light according to the applied voltage, is used as a liquid crystal, it is unnecessary to use the polarized light as for the readout light. Therefore, a polarizer and an analyzer become unnecessary, thereby making it possible to simplify the structure of a picture information reproducing device.

Figure 3:
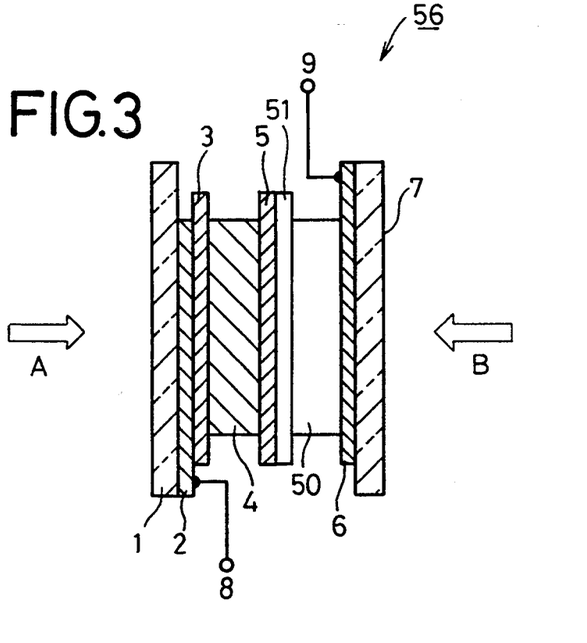
FIG. 3 is a cross-sectional view for explaining another PROM element with a liquid crystal used for a picture information memory device and a picture information reproducing device according to the present invention.

As shown in FIG. 3, a PROM element with liquid crystal 50' in which a reflection layer 51 is disposed between the liquid crystal layer 50 and the charge generating and holding layer 4, may be used. As the reflection layer 51, a stacked layer of $TiO_2$ and $SiO_2$ is used. A picture information write-in light is directed onto the charge generating and holding layer 4 from the direction of an arrow A to record the picture information. A readout light is directed onto the liquid crystal layer 50 from the direction of an arrow B, and then is reflected by the reflection layer 51, and finally is emitted backward toward the opposite direction of the arrow B to reproduce the picture information. With this structure, because the readout light does not pass through the charge generating and holding layer 4, even though the wavelength of the readout light is chosen to be any value, the distribution state of the polarized charges in the charge generating and holding layer 4 is not changed.

Additionally, if the liquid crystal layer 50 has a sufficient high insulating characteristic and the polarized charges can be held on the surface of the charge generating and holding layer 4 by the liquid crystal layer 50, one of or both of the insulating layers 3 and 5 may not be provided.

A description will next be made of a picture information memory device and a picture information reproducing device using any one of the PROM element 16 shown in FIG. 1, the PROM element with liquid crystal 56 shown in FIG. 2, and the PROM element with liquid crystal 56' shown in FIG. 3, and a method of recording and reproducing picture information by using these devices.

FIRST EMBODIMENT

Figure 4:
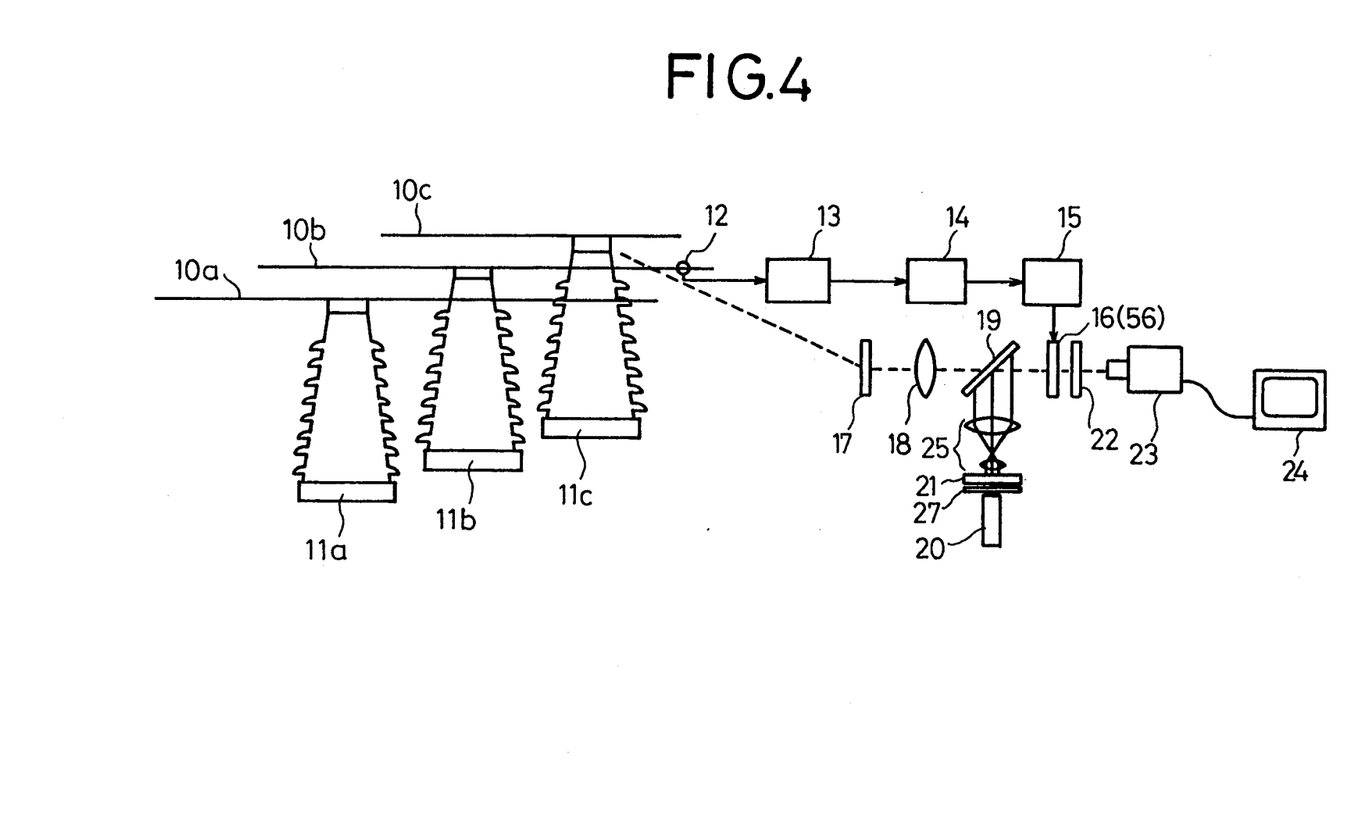
FIG. 4 is a schematic diagram for explaining a picture information memory device and a picture information reproducing device according to a first embodiment of the present invention.

Referring to FIG. 4, a description will be made of a method of recording and reproducing, as picture information, spark discharge patterns developed at a high voltage insulator by a picture information memory device and a picture information reproducing device according to a first embodiment of the present invention.

When an insulation failure occurs at a high voltage insulator of a transmission line, a spark discharge is produced. The spark discharge is periodically generated at a frequency twice that of a current flowing in the transmission line. Even when it is desired to record the spark discharge patterns during the day, the rays of the sun are also received. Therefore, the spark discharge patterns cannot be clearly recorded. By using the picture information recording device and the picture information reproducing device according to the present invention to avoid such inconvenience, such patterns can be distinctly recorded in the charge generating and holding layer 4.

Three power lines 10a through 10c are respectively supported by high voltage insulator 11a through 11c. A current detector 12 is mounted on the power line 10b, and the waveform of current which flows through the power line 10b is detected by the current detector 12. The detected current waveform is then amplified by an amplifier 13, followed by being supplied to a double wave generator 14 from which a signal of a frequency twice that of the detected current is generated. The signal thus generated is then supplied to a high voltage alternating-current generator 15 so as to generate a high voltage alternating-current bias voltage which is identical in phase to the current flowing through the power line 10b and whose frequency is twice that of the current. Thereafter, the high voltage alternating-current bias voltage generator 15 applies the generated high voltage alternating-current bias voltage to a PROM element 16, a PROM element with liquid crystal 56, or a PROM element with liquid crystal 56'.

Light produced by the generated spark discharge is directed onto the PROM element 16, the PROM element with liquid crystal 56, or the PROM element with liquid crystal 56' through a shutter 17, an image formation lens system 18 and a halfmirror 19. Since the alternating-current bias voltage synchronized with the spark discharge which repeatedly appears at a regular period, is applied to the PROM element 16, the PROM element with liquid crystal 56, or the PROM element with liquid crystal 56', only a picture produced by the spark discharge is recorded in the PROM element 16, the PROM element with liquid crystal 56, or the PROM element with liquid crystal 56' without recording the rays of the sun therein. As a result, only the picture based on the spark discharge can be distinctly stored in the PROM element 16, the PROM element with liquid crystal 56, or the PROM element with liquid crystal 56' even if the rays of the sun fall on the PROM element 16, the PROM element with liquid crystal 56, or the PROM element with liquid crystal 56'. In the present embodiment, the frequency at which the spark discharge is produced and its phase are detected by the current detector 12 disposed on the power line 10b. It is, however, unnecessary to provide the current detector 12 if the frequency of the current flowing through the power line 10b and the phase of the current have already been known.

A description will next be made of a reproduction optical system for reproducing the picture information recorded in the PROM element 16, the PROM element with liquid crystal 56, or the PROM element with liquid crystal 56'.

When it is desired to reproduce the recorded picture information, the shutter 17 is closed and the high voltage alternating-current voltage generator 15 is turned off.

Further, readout light is emitted from a laserbeam source 20. Light, which does not cause a photoconductive effect in a $Bi_{12}SiO_{20}$ crystal used for the PROM element 16, the PROM element with liquid crystal 56, or the PROM element with liquid crystal 56', for example, light having a wavelength of 633 nm, is used as the readout light. Thereafter, the readout light emitted from the laser-beam source 20 is linearly polarized by a polarizer 27. Then, the readout light passes through a reproducing light shutter 21. Further, the readout light is brought to be an enlarged parallel light beam by a beam expander 25 comprised of an expander lens and a collimator lens. Thereafter, the beam passes through the halfmirror 19 so as to be directed onto the PROM element 16, the PROM element with liquid crystal 56, or the PROM element with liquid crystal 56'.

The readout light which has been directed onto the PROM element 16, the PROM element with liquid crystal 56, or the PROM element with liquid crystal 56', becomes elliptically polarized light having an ellipticity according to the picture information which has been recorded in the PROM element 16, the PROM element with liquid crystal 56, or the PROM element with liquid crystal 56', after which the polarized light is emitted from the PROM element 16, the PROM element with liquid crystal 56, or the PROM element with liquid crystal 56'. Accordingly, the picture information which has been recorded in the PROM element 16, the PROM element with liquid crystal 56, or the PROM element with liquid crystal 56', is reproduced as an optical image having a light intensity distribution corresponding to the recorded picture information by causing the reading light to pass through an analyzer 22 disposed in the rearward of the PROM element 16, the PROM element with liquid crystal 56, or the PROM element with liquid crystal 56'. Then, the optical image is recorded by a TV camera 23 so as to be displayed on a monitor 24.

With this arrangement, the picture information which has been once recorded in the PROM element 16, the PROM element with liquid crystal 56, or the PROM element with liquid crystal 56', can be immediately reproduced, thereby making it possible to realize a portable picture recording and reproducing device. Even if the rays of the sun fall on the PROM element during the day, a determination can be immediately made as to whether or not discharge faults have occurred in a high voltage insulator, a transformer, etc.

In this case, if a liquid crystal, such as PDLL, which changes the transmissivity of light, is used for the liquid crystal layer 50 of the PROM element with liquid crystal 56 and PROM element with liquid crystal 56', the polarizer 27 and the analyzer is unnecessary.

SECOND EMBODIMENT

Figure 5:
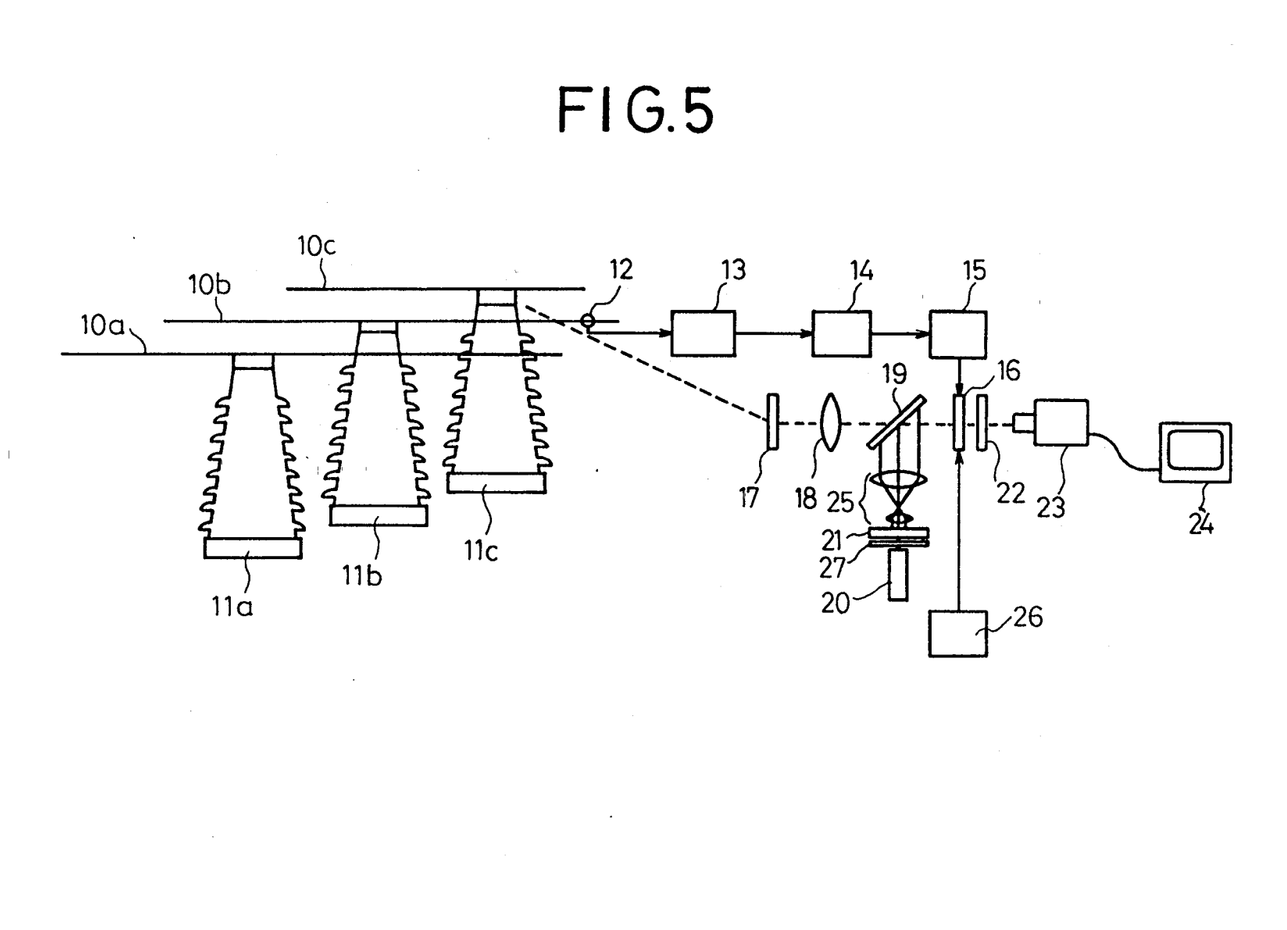
FIG. 5 is a schematic diagram for explaining a picture information memory device and a picture information reproducing device according to a second embodiment of the present invention.

Referring to FIG. 5, a second embodiment of the present invention will now be explained. The present embodiment differs from the first embodiment in that a direct-current voltage generator 26 capable of applying a direct-current bias voltage to the PROM element 16, the PROM element with liquid crystal 56, or the PROM element with liquid crystal 56' is further provided. The other constitution is identical to those employed in the first embodiment.

A direct-current bias voltage as well as the alternating-current bias voltage can be applied to the PROM element 16, the PROM element with liquid crystal 56, or the PROM element with liquid crystal 56' by further providing the direct-current voltage generator 26 in addition to the high voltage alternating-current voltage generator 15. Thus, picture information of the background insulators 11a through 11c and the background power lines 10a through 10c can also be recorded as well as picture information of the periodically-generated spark discharge in a state in which both information is superimposed on each other, thereby making it possible to accurately recognize the position where the spark discharge is now generating.

In the present embodiment, the alternating-current bias voltage is first applied to the PROM element 16, the PROM element with liquid crystal 56, or the PROM element with liquid crystal 56' from the high voltage alternating-current voltage generator 15 so as to record spark discharge patterns. Then, the direct-current bias voltage may be applied to the PROM element 16, the PROM element with liquid crystal 56, or the PROM element with liquid crystal 56' by the direct-current voltage generator 26 so as to superimposedly record picture information of the background insulators 11a through 11c and the background power lines 10a- through 10c in the PROM element 16, the PROM element with liquid crystal 56, or the PROM element with liquid crystal 56'. Alternatively, the alternating-current bias voltage and the direct-current bias voltage may be simultaneously applied to the PROM element 16, the PROM element with liquid crystal 56, or the PROM element with liquid crystal 56' by the high voltage alternating-current voltage generator 15 and the direct-current voltage generator 26 so as to simultaneously record the spark discharge patterns and picture information of the background insulators 11a through 11c and the background power lines 10 through 10c.

THIRD EMBODIMENT

Figure 6:
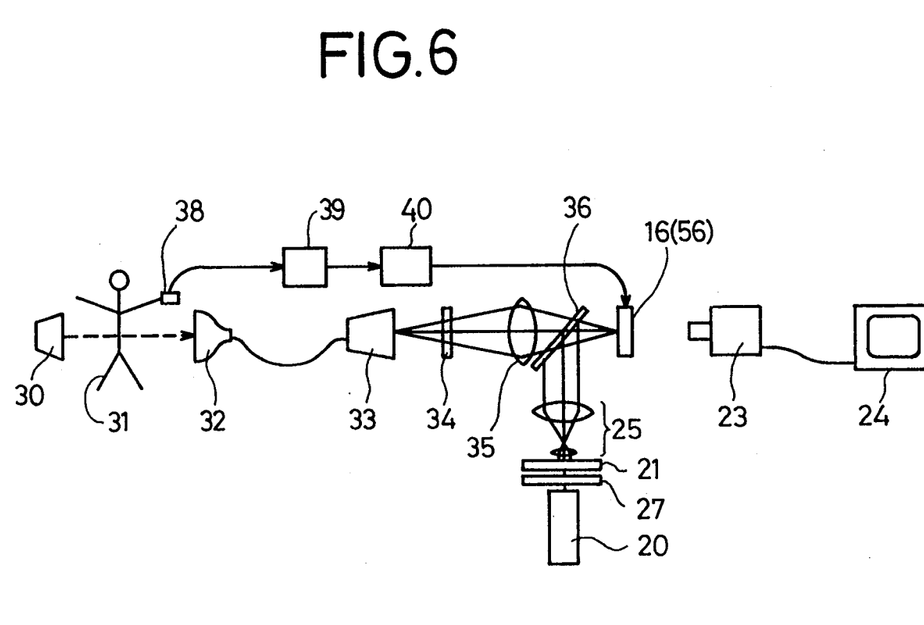
FIG. 6 is a schematic diagram for explaining a picture information memory device and a picture information reproducing device according to a third embodiment of the present invention.

Referring to FIG. 6, a description will be made of a method recording and reproducing, as picture information, a blood vessel image obtained as a transmitted image of a human body by a picture information memory device and a picture information reproducing device according to a third embodiment of the present invention.

A blood flow in the blood vessel varies at a period corresponding to the heartbeat. When the blood vessel is recorded as an X-ray image, it is represented as a concentration image corresponding to the quantity of the blood flow. Accordingly, the X-ray image of the blood vessel is represented as an image in which the strength of the blood vessel varies according to the heartbeat. When, on the other hand, the blood vessel is photographically recorded by an X-ray exposure device, the blood vessel is photographically recorded together with a static image of such as a skeleton or the like. As a result, only the image of the blood vessel could not be distinctly recorded. If the picture information memory device and the picture information reproducing device according to the present invention are used in this case, then only the blood vessel image having the periodicity can be distinctly recorded, thereby making it possible to contribute to the diagnosis of various diseases.

A subject human body 31 is irradiated with X-rays from an X-ray source 30. Then, an X-ray transmitted image is recorded by an X-ray camera 32 so as to display the recorded X-ray transmitted image on a display unit 33. The image of the displayed blood vessel is represented in the form of an image in which the strength of the blood vessel is varied at a period corresponding to the heartbeat. The blood vessel image is projected onto the PROM element 16, the PROM element with liquid crystal 56, or the PROM element with liquid crystal 56' through a shutter 34, an image formation lens system 35 and a halfmirror 36.

The waveform of the pulse of the human body 31 is measured by a pulse waveform measuring device 38. A signal outputted from the pulse waveform measuring device 38 is supplied to a phase adjuster 39. The phase adjuster 39 forms a pulse signal whose phase is delayed for a proper time interval from the measured pulse, and supplies it to an alternating-current high-voltage source 40 from which an alternating-current bias voltage synchronized with the signal outputted from the phase adjuster 39 is generated so as to be applied to the PROM element 16, the PROM element with liquid crystal 56, or the PROM element with liquid crystal 56'.

With this arrangement, the phase of the alternating-current bias voltage applied to the PROM element 16, the PROM element with liquid crystal 56, or the PROM element with liquid crystal 56' can be made coincident with that of a blood flow at an observation position even if a time delay occurs in the flow of the blood flowing in the blood vessel. It is, therefore, possible to distinctly record only the image of the blood vessel in the PROM element 16, the PROM element with liquid crystal 56, or the PROM element with liquid crystal 56'.

A reproduction optical system for reproducing the picture which has been recorded in the PROM element 16, the PROM element with liquid crystal 56, or the PROM element with liquid crystal 56', is identical to that employed in the first embodiment.

Even in the case of the present embodiment, the recorded picture can be subjected to the optical image processing such as the optical Fourier transformation, if necessary.

FOURTH EMBODIMENT

Figure 7:
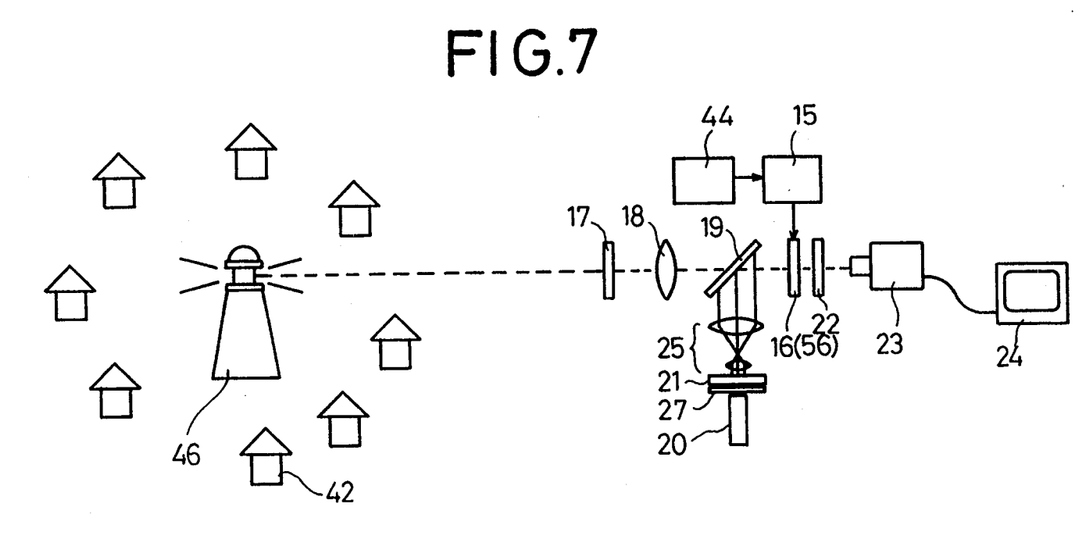
FIG. 7 is a schematic diagram for explaining a picture information memory device and a picture information reproducing device according to a fourth embodiment of the present invention.

Referring to FIG. 7, a method of separating, from city lights, light such as light produced from a lighthouse and signal lamp which flash or blink at its inherent period, and recording and reproducing the separated light by making use of a picture information memory device and a picture information reproducing device according to a fourth embodiment of the present invention, will be explained. A device employed in the present embodiment is called a "navigational support device".

When an aircraft flies in the sky of the town or when it lands on an airport in the town, for example, light produced from a navigational supporting lighthouse, a navigational supporting signal lamp and the like are separated and detected from the lights of the town. Information about the detected light is made useful for the control of flight of the aircraft.

A navigational supporting lighthouse 40 is flashed at a predetermined frequency. Light emitted from the lighthouse 40 is directed on a PROM element 16, the PROM element with liquid crystal 56, or the PROM element with liquid crystal 56' through a shutter 17, an image formation lens system 18 and a halfmirror 19. Then, an alternating-current high voltage source 15 applies an alternating-current bias voltage whose frequency is identical to that of the light emitted from the lighthouse 40 to the PROM element 16, the PROM element with liquid crystal 56, or the PROM element with liquid crystal 56'. The phase of the alternating-current bias voltage is adjusted based on a signal outputted from a phase adjuster 44 disposed before the alternating-current high voltage source 15.

Since the alternating-current bias voltage having the frequency identical to the flashing frequency of light emitted from the lighthouse 40 is applied to the PROM element 16, the PROM element with liquid crystal 56, or the PROM element with liquid crystal 56', only the image of the light emitted from the lighthouse 40 is recorded in the PROM element 16, the PROM element with liquid crystal 56, or the PROM element with liquid crystal 56' without recording the light of the town 42.

Having now fully described the invention, it will be apparent to those skilled in the art that many changes and modification can be made without departing from the spirit or scope of the invention as set forth herein.

What is claimed is:

1. A picture information memory device comprising:
   picture information memory means for generating electric charges corresponding to the intensity of write-in light incident thereon, and for holding said generated electric charges as charges having a predetermined polarity;
   exposing means for exposing said picture information memory means to light from an object, wherein an intensity of a portion of said light from said object varies at a regular frequency;
   means for determining said regular frequency at which said intensity varies;
   alternating-current bias voltage applying means for applying an alternating-current bias voltage having a desired frequency to said picture information memory means, said desired frequency being chosen to match said regular frequency,
   whereby electric charges generated by the portion of said object light, the intensity of which varies at the same frequency as that of said alternating-current bias voltage, are selectively accumulated from the entirety of electric charges generated by said object light incident on said picture information memory means, and held as said charges in said picture information memory means.

2. A picture information memory device as recited in claim 1, further comprising:
   frequency detecting means for detecting said regular frequency at which the intensity of said portion of said object light varies, and
   wherein said alternating-current bias voltage applying means applies said alternating-current bias voltage at the same frequency as said regular frequency.

3. A picture information memory device as recited in claim 1 or 2, further comprising:
   phase adjusting means for adjusting the phase of said alternating-current bias voltage.

4. A picture information memory device as recited in claim 1, or 2, further comprising:
   direct-current bias voltage applying means for applying a direct-current bias voltage to said picture information memory means.

5. A picture information memory device as recited in claim 1 or 2,
   wherein said picture information memory means comprises a spatial light modulating means for generating electric charges corresponding to the intensity of write-in light incident thereon, for holding said generated electric charges as charges having a predetermined polarity, and for varying a polarization state of readout light incident thereon according to said charges.

6. A picture information memory device as recited in claim 5,
   wherein said spatial light modulating means comprises an element for generating electric charges corresponding to the intensity of write-in light incident thereon due to a photoconductive effect, for holding said generated electric charges as charges having a predetermined polarity, and for varying a polarization state of readout light incident thereon according to said charges due to Pockels effect.

7. A picture information memory device as recited in claim 6, further comprising:
   a liquid crystal layer capable of changing the polarization state or the transmissivity of said readout light according to said charges.

8. A picture information memory device as recited in claim 1 or 2,
   wherein said picture information memory means comprises a memory layer of a material having a photoconductive effect and a readout layer of a liquid crystal.

9. A picture information reproducing device, comprising:
   a spatial light modulating means for generating electric charges corresponding to an intensity of write-in light incident thereon, for holding said generated electric charges as charges having a predetermined polarity, and for modulating readout light incident thereon according to said charges;
   first exposing means for exposing said spatial light modulating means to light from an object, wherein an intensity of a portion of said light from said object varies at a regular frequency;
   means for determining said regular frequency at which said intensity varies;
   alternating-current bias voltage applying means for applying an alternating-current bias voltage having a desired frequency to said spatial light modulating means, said desired frequency being chosen to match said regular frequency;
   second exposing means for exposing said spatial light modulating means to readout light; and
   readout light detecting means for detecting said readout light emitted from said spatial light modulating means,
   whereby electric charges generated by the portion of said object light, the intensity of which varies at the same frequency as that of said alternating-current bias voltage, are selectively accumulated from the entirety of electric charges generated by said object light incident on said spatial light modulating means, and held as said charges in said spatial light modulating means, and picture information from said portion of said object light, the intensity of which varies at said same frequency as that of said alternating-current bias voltage, is selectively detected by detecting said emitted readout light modulated according to said charges.

10. A picture information reproducing device as recited in claim 9, further comprising:
    frequency detecting means for detecting said regular frequency at which the intensity of said portion of said object light varies, and
    wherein said alternating-current bias voltage applying means applies said alternating-current bias voltage at the same frequency as said regular frequency.

11. A picture information reproducing device as recited in claim 9 or 10, further comprising:
    phase adjusting means for adjusting the phase of said alternating-current bias voltage.

12. A picture information reproducing device as recited in claim 9 or 10, further comprising:

direct-current bias voltage applying means for applying a direct-current bias voltage to said spatial light modulating means.

13. A picture information reproducing device as recited in claim 9 or 10,
wherein said spatial light modulating means comprises a spatial light modulating means for generating electric charges corresponding to the intensity of write-in light incident thereon, for holding said generated electric charges as charges having a predetermined polarity, and for varying the polarization state of readout light incident thereon according to said charges.

14. A picture information reproducing device as recited in claim 13,
wherein said spatial light modulating means comprises an element for generating electric charges corresponding to the intensity of write-in light incident thereon due to a photoconductive effect, for holding said generated electric charges as charges having a predetermined polarity, and for varying the polarization state of readout light incident thereon according to said charges due to a Pockels effect.

15. A picture information reproducing device as recited in claim 14, further comprising:
a liquid crystal layer capable of changing the polarization state or the transmissivity of said readout light according to said charges.

16. A picture information reproducing device as recited in claim 9 or 10,
wherein said spatial light modulating means comprises a spatial light modulating means for generating electric charges corresponding to the intensity of write-in light incident thereon, for holding said generated electric charges as charges having a predetermined polarity, and for varying the transmissivity of readout light incident thereon according to said charges.

17. A picture information reproducing device as recited in claim 9 or 10,
wherein said spatial light modulating means comprises a memory layer of a material having a photoconductive effect and a readout layer of a liquid crystal.

* * * * *